United States Patent
Kulik et al.

(10) Patent No.: US 8,306,187 B2
(45) Date of Patent: Nov. 6, 2012

(54) OPTIMAL DETECTOR POSITION FOR GAMMA BACKSCATTER

(75) Inventors: Alex Kulik, Sugar Land, TX (US); Alexander Joseph Esin, Sugar Land, TX (US); Nikolay Baturin, Sugar Land, TX (US); Hai Wang, Sugar Land, TX (US)

(73) Assignee: Thermo Fisher Scientific Inc., Sugar Land, TX (US)

( * ) Notice: Subject to any disclaimer, the term of this patent is extended or adjusted under 35 U.S.C. 154(b) by 242 days.

(21) Appl. No.: 12/852,226

(22) Filed: Aug. 6, 2010

(65) Prior Publication Data

US 2012/0033792 A1    Feb. 9, 2012

(51) Int. Cl.
*G01B 15/02* (2006.01)
(52) U.S. Cl. .......................... 378/89; 378/86
(58) Field of Classification Search ............ 378/54, 378/86–90
See application file for complete search history.

(56) References Cited

U.S. PATENT DOCUMENTS
2008/0226026 A1* 9/2008 Kulik et al. .................. 378/52

FOREIGN PATENT DOCUMENTS
EP  1921435 A3  8/2011
SU  1390529 A1  4/1988

OTHER PUBLICATIONS

Combined Search and Examination Report for GB Application No. GB1113356.8 dated Nov. 24, 2011 (6 pages).

* cited by examiner

*Primary Examiner* — Hoon Song
(74) *Attorney, Agent, or Firm* — Osha • Liang LLP

(57) ABSTRACT

A method for determining the density of a fluid that includes disposing a gamma-ray source proximate to a vessel containing the fluid is provided. The optimal position of a gamma-ray detector with respect to the gamma-ray source is determined. A gamma-ray detector is position at the optimal position, and the density of the fluid is measured.

18 Claims, 7 Drawing Sheets

OPTIMAL DETECTOR POSITION FOR GAMMA BACKSCATTER

BACKGROUND OF INVENTION

1. Field of the Invention

Embodiments disclosed herein relate generally to a method for measuring the density of a fluid in a vessel using gamma radiation. Specifically, embodiments disclosed herein relate to a method for optimizing the measurement of the density of a fluid in a vessel by detecting the intensity of gamma rays backscattered by the fluid from a gamma-ray source.

2. Background

Gamma rays have been used to measure the density and level of fluids in a vessel by using a gamma-ray source positioned opposite or near a gamma-ray detector. Gamma-ray density and level measurements are useful where the materials measured are hazardous, extremely hot, or where direct contact measurements are otherwise not possible. Additionally, the source and detector are mounted outside the vessel, and no modification to the vessel is required. Gamma rays emitted by a source may be absorbed or attenuated by the vessel and the material in the vessel. The strength of the gamma radiation reaching a detector may be used to indicate the density or level of a fluid in a vessel based upon the intensity of the source.

When measuring fluid level, for example, gamma-ray emitters and/or detectors may be positioned on or near a vessel, where the presence or absence of a signal (or a nominal low signal) may indicate the presence or absence of a fluid near the source and detector. With respect to fluid density, fluid near the gamma-ray source and detector may absorb or attenuate gamma rays emitted by the source. For example, a high radiation count may indicate a low fluid density while a low count may indicate a high fluid density.

A through-transmission gamma-ray densitometer may contain a housing mounted on vessel which contains a fluid. A source of gamma radiation is located on one side of the vessel and a gamma radiation detector is located on the opposite side of the vessel. The radiation provided by the source is a constant intensity over a long period of time (random intensity over a finite period) of gamma-ray emissions. The gamma rays are transmitted through the vessel wall, the fluid within the vessel, again through the vessel wall, and to the detector. The detector may be, for example, a crystal of sodium or cesium iodide (thallium activated) or other material capable of scintillating under irradiation and may include an electron photomultiplier tube for converting light flashes of the scintillation of the crystal into an electrical pulse.

A primary variable with respect to the amount of gamma rays emitted from the source that reach the detector is the fluid contained within the vessel. A percentage of the gamma rays emitted by the source are absorbed or attenuated by fluid and, therefore, do not reach the detector. Thus, the counting rate of the output signal from a photo multiplier tube of a detector may be related to the density of fluid through which the rays must pass to reach the detector and the intensity of the gamma radiation source.

In practice, through-transmission density measurements using gamma rays are viable only for limited vessel sizes and/or fluid densities. For example, for a similar sized source, at higher fluid densities, the fluid may absorb more gamma rays, thus resulting in fewer gamma rays reaching the detector. Similarly, as vessel size is increased, gamma rays must pass through a greater quantity of material (vessel and fluid) absorbing the gamma rays, resulting in fewer gamma rays reaching the detector. Therefore, through-transmission gamma-ray density measurements may be viable only for vessels up to about 1 meter in diameter.

Vessel wall thickness may also limit the effectiveness of gamma-ray density measurements. As vessel walls absorb and attenuate gamma rays in a manner similar to fluids, and a higher wall thickness may result in fewer gamma rays reaching the detector. Vessel wall thickness may be determined by guidelines, such as by the American Society of Mechanical Engineers (ASME). Vessel wall thickness may also be determined on other specifications, such as when the required thickness is based upon operating pressure and the nature of the fluid (corrosive, erosive, reactive, etc.). Furthermore, current safety margins for vessel wall thickness may increase and may further limit the effectiveness of through-transmission measurements.

When employing gamma-rays for density measurements, lower count rates may result in a greater rate of error or may require a larger gamma radiation source to maintain a desired accuracy. In addition, as vessel size increases, detector size may have to be increased to maintain a constant count rate. Regardless, increasing the size of the source and/or the size of the detector will invariably increase costs.

To overcome the thickness, size, and density limitations, the intensity of the gamma-ray source may be increased, thus resulting in a measurable quantity of gamma rays reaching the detector. However, cost, safety, multi-unit effectiveness, and security may limit the source intensity that may be used. The use of a radioactive source creates personnel safety and environmental concerns and requires lead or tungsten shielding to protect personnel, special handling precautions and equipment, as well as disposal and remediation procedures. Furthermore, because gamma rays are produced from a point source and not a directional source, as the size of the source increases, the amount of shielding required to contain the radiation in directions other than into the vessel must be increased, thus adding further to the cost.

With respect to multi-unit effectiveness, a chemical plant may desire to use gamma-ray level and density gages on multiple vessels. However, as the number of gages increases or the intensity of gamma-ray sources increases, cross-talk between gamma-ray sources and detectors on adjacent vessels may occur, resulting in decreased effectiveness and potentially erroneous readings.

Regarding security, due to growing worldwide concerns about the proliferation and possible smuggling or other transport of radioactive nuclear materials, state, local, and national governments regulate facility security requirements based upon the total amount of radioactive material that may be present at a single site. For example, the State of Texas requires additional security measures (e.g., background checks, accessibility, etc.) at facilities where the total Curie count exceeds 27 Curie, where the total Curie count is based upon a sum of all radioactive sources at the facility. Thus, use of larger sources may result in an increased need for security at an additional cost.

Accordingly, there exists a need for optimized gamma-ray density measurements that may be used on large vessels. Additionally, there exists a need for optimized non-contact density gages that require lower intensity radiation sources.

SUMMARY OF INVENTION

In one aspect, embodiments disclosed herein relate to a method for determining the density of a fluid. The method includes disposing a gamma-ray source proximate to a vessel having the fluid disposed therein, determining an optimal position of a gamma-ray detector with respect to the gamma-ray source, disposing a gamma-ray detector at the optimal position, and measuring the density of the fluid.

In one aspect, embodiments disclosed herein relate to a method for optimizing the position of a gamma-ray detector to determine the density of a fluid in a vessel, the method includes disposing a gamma-ray source proximate a vessel having the fluid disposed therein, determining an optimal position of a gamma-ray detector with respect to the gamma-ray source, disposing at least one gamma-ray detector at the optimal position with respect to the gamma-ray source, and measuring the density of the fluid from the gamma-ray detector.

Other aspects and advantages of the invention will be apparent from the following description and the appended claims.

DETAILED DESCRIPTION

In one aspect, embodiments disclosed herein relate to a method for measuring the density of a fluid in a vessel using gamma rays. In other aspects, embodiments disclosed herein relate to a method for optimizing the measurement of the density of a fluid in a vessel using gamma rays. In particular, embodiments disclosed herein relate to a method of optimizing the measurement of the density of a fluid in a vessel by detecting the intensity of gamma rays backscattered by the fluid from a gamma-ray source.

As used herein, "backscatter" may refer to the deflection of gamma rays from an original direction. In some embodiments, the backscatter may be isotropic, such as where the gamma rays are scattered randomly in various directions. Backscattering occurs due to Compton scattering.

As used herein, "fluid" refers to gases, liquids, and solids that may be contained within a vessel. Fluids may include aqueous liquids, organic liquids, single-phase systems, and multi-phase systems such as foams, emulsions, and fluidized particles.

Figure 1:
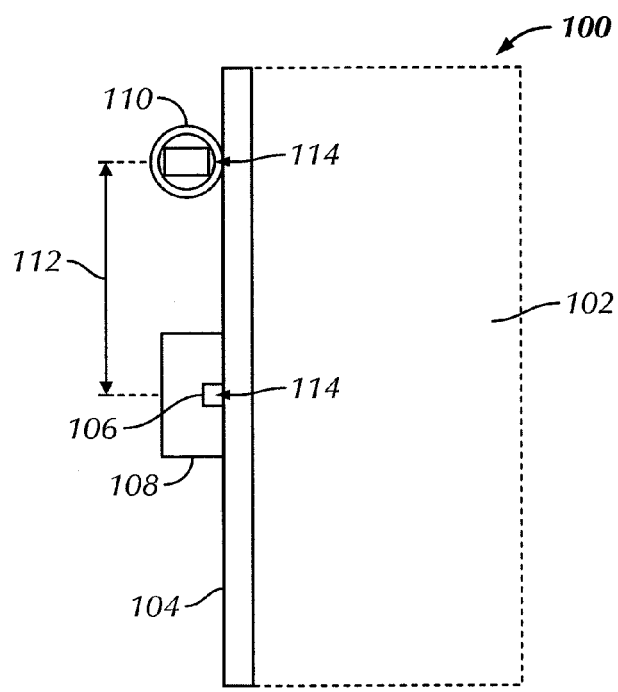
FIG. 1 is a schematic drawing of a gamma-ray density measurement system in accordance with embodiments disclosed herein.

Referring to FIG. 1, a schematic of the gamma-ray source and detector in accordance with one or more embodiments is shown. The source/detector system 100 has a fluid 102 contained within vessel walls 104. A gamma-ray source head 106 is mounted onto the vessel wall 104. The gamma-ray source head 106 has shielding 108 for safety concerns and to limit or admonish gamma radiation not contributing to the prescribed measurements. A gamma-ray detector 110 is mounted on the vessel wall at a position 112 relative to the gamma-ray source head 106. In accordance with embodiments disclosed herein, position 112 is measured from the center of the gamma-ray source head 106 to the center of the gamma-ray detector 110. However, one of ordinary skill in the art will recognize that the relative positions of the gamma-ray source and gamma-ray detector may be determined by other methods. For example, the position could be determined by referencing to some external point.

In accordance with one or more embodiments disclosed herein, the gamma-ray source head 106 emits gamma radiation 114 through the vessel wall 104 and into the fluid 102. The gamma radiation 114 is then backscattered from the fluid 102 and detected by the gamma-ray detector 110.

Figure 2A:
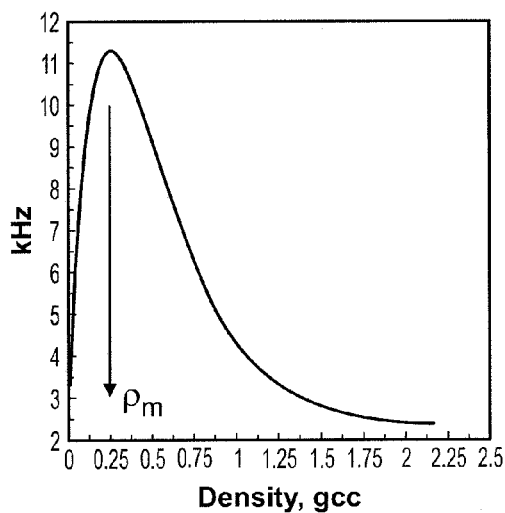
FIG. 2(a) is a chart depicting the counting rate of backscatter as a function of density in accordance with embodiments disclosed herein.

The gamma-ray detector 110 operates by measuring a count rate directly related to the amount of gamma-radiation received. FIG. 2(a) is an empirical chart depicting the counting rate of backscatter from a detector 110 as a function of density of the fluid 102 in accordance with embodiments disclosed herein. In this illustrative embodiment, the wall thickness was 1.5 inches. As can be seen from FIG. 2(a), a density of 0.75 gcc (grams per cubic centimeter) may produce the same count rate as that of a density of 0.1 gcc. Therefore, the operational range may be divided into two regions.

For example, embodiments disclosed herein may be limited to a low density region, as represented by densities located before the maximum of the curve in FIG. 2(a). Similarly, one or more embodiments disclosed herein may be limited to a high density region, represented by densities located after the maximum of the curve in FIG. 2(a). In FIG. 2(a), the density at which the counting rate is a maximum is noted as $\rho_m$. Specifically, in many industrial applications, for example refineries, the fluid may be mostly oil having a density of 0.8 gcc or higher. As a further example, industrial applications in mining fluids may be mostly water having a density of 1.0 gcc or above.

Figure 2B:
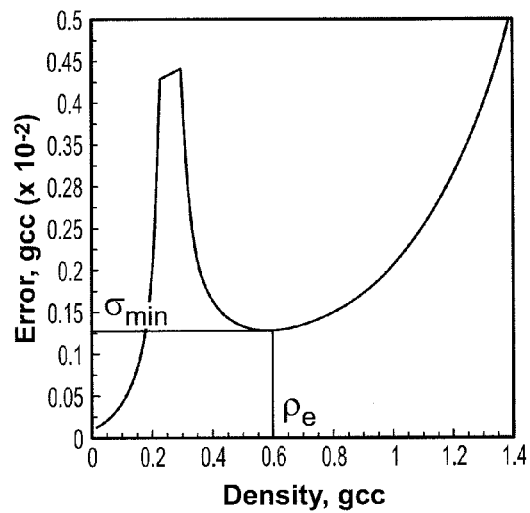
FIG. 2(b) is a chart depicting the density measurement error of gamma-ray detection as a function of density in accordance with embodiments disclosed herein.

FIG. 2(b) is the density measurement error of gamma-ray detection as a function of density in accordance with embodiments disclosed herein. The precision of the density measurement, or the density measurement error, may depend on the slope of the curve shown in FIG. 2(a). For example, the resolution $\sigma_p$ may be expressed as:

$$\sigma_\rho = \frac{\sqrt{f/\tau}}{\left|\frac{df}{d\rho}\right|} \tag{1}$$

where f represents the counting rate, $\rho$ is the density and $\tau$ is the time constant.

As can be seen in FIG. 2(b), in accordance with one or more embodiments of the methods disclosed herein, the density measurement loses precision as the density approaches the density at which the counting rate is a maximum $\rho_m$. Also, in this particular illustrative embodiment, given the lower count rates at densities greater than 1.5 gcc shown in FIG. 2(a), the error in the density measurement at densities greater than 1.5 gcc may have a significant loss in precision.

However, in the aforementioned high density range, there may exist a point where the error in the density measurement is a minimum. In FIG. 2(b), in accordance to the embodiments of the methods disclosed herein, the density of the highest precision $\rho_e$ with the minimal error in density measurement $\sigma_{min}$ is shown.

As stated previously, the illustrative curves shown in FIGS. 2(a) and 2(b) are for a specific detector position and vessel wall thickness. The exact shape of the curves in FIG. 2 may be determined by the detector position and vessel wall thickness.

In accordance with embodiments disclosed herein, the ability to measure the back scattered gamma rays may depend on the density of the fluid, vessel wall thickness, and source-detector distance. Therefore, given a specific source-detector distance, there may exist a density region where the density measurements are very effective, less effective, or not effective. For example, as demonstrated in FIG. 2(b), the measurement of the density is very effective around a density of 0.6 gcc, less effective for densities between 0.3-0.4 gcc, and not effective when the density is greater than 2.25 gcc.

Analogously, given a specific density interval measurement of interest, one or more embodiments disclosed herein may make possible the determination of the optimal distance between the gamma-ray source and gamma-ray detector for the most accurate density measurement. At the same time, the optimal distance between the gamma-ray source and gamma-ray detector may, according to one or more embodiments disclosed herein, determine which, if any, density ranges may not be accurately determined.

Figure 3:
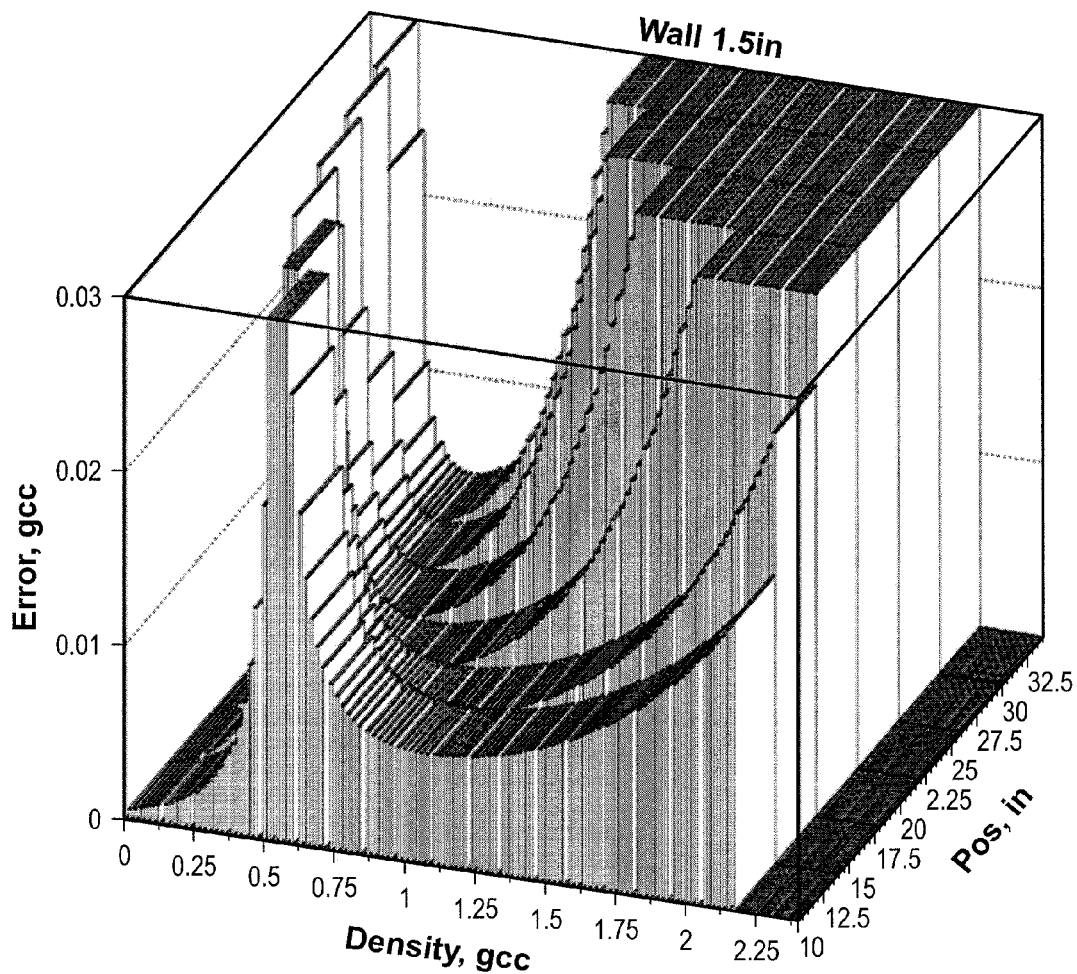
FIG. 3 is a three dimensional chart of the density measurement error of gamma-ray detection as a function of density and relative position of the detector in accordance with embodiments disclosed herein.

FIG. 3 is a three dimensional chart of the density measurement error of gamma-ray detection as a function of density and relative position of the detector in accordance with embodiments disclosed herein. The illustrative embodiment of FIG. 3 was determined by using a 100 mCi cesium-137 source and the experimentally measured dependence on the density for different detector positions, with a wall thickness of 1.5 inches and time constant $\tau$ of 32 seconds. Accordingly, there may exist an optimal detector position for any given density.

FIG. 3 demonstrates that with a vessel wall thickness of 1.5 inches, the different positions of the gamma-ray detector relative to the gamma-ray source determine the specific values of the illustrative curves shown in FIG. 2. However, the overall shape of the curves illustrated in FIG. 2 remains the same.

One or more embodiments of the present invention may use charts similar to FIG. 3 to determine the optimal detector position for one or more given densities. As can be seen from FIG. 3, there is an optimal detector position for every given density. In general, a closer position of the gamma-ray detector with respect to the gamma-ray source may offer a better precision and a wider operational range for densities similar to that of water. However, further positions offer better precision for densities in the range 0.5-0.7 gcc. At densities lower than the density at which the counting rate is a maximum $\rho_m$ the precision may be better than at densities higher than the density at which the counting rate is a maximum $\rho_m$. However, in such a case, the closer position may offer a larger operation range, for example 0-0.4 gcc.

Figure 4:
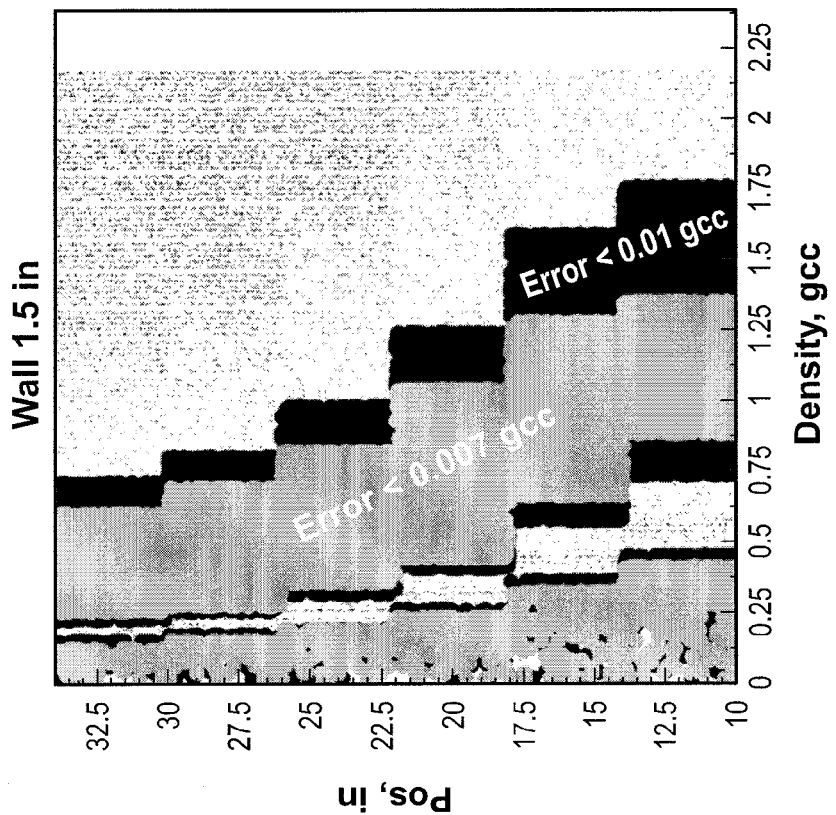
FIG. 4 is a two dimensional projection of FIG. 3 in accordance with embodiments disclosed herein.

FIG. 4 is a two-dimensional projection of FIG. 3 in accordance with embodiments disclosed herein. With a vessel wall thickness of 1.5 inches, the optimal position of the gamma-ray detector may be determined, given the density. FIG. 4 illustrates shaded regions where the density measurement error is less than 0.007 gcc and the density error measurement is less than 0.01 gcc. In addition, an operational range of the gamma-ray source/detector system may be determined For example, given an estimate of density and a known vessel wall thickness, an optimal relative position of the gamma-ray detector with respect to the gamma-ray source may be selected. Accordingly, a range of the precision of the density measurement may be determined. Alternatively, the density estimate and known vessel thickness may be used to determine an optimal range of the relative position of the gamma-ray detector relative the to gamma-ray source to maximize the precision of the density measurement.

Figure 5:
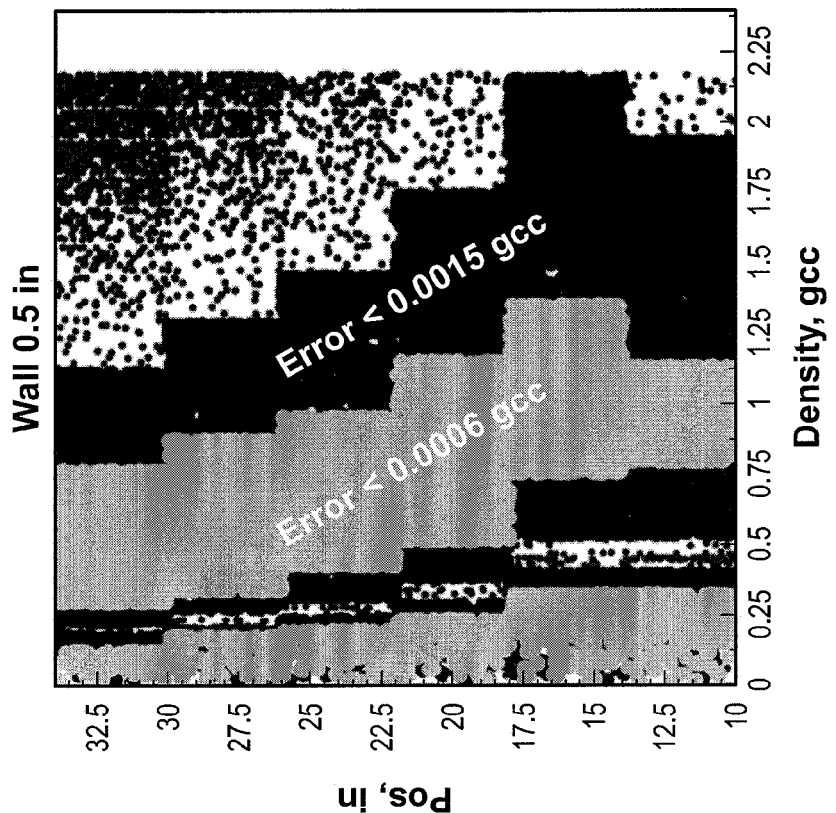
FIGS. 5-7 are two dimensional projections with different vessel wall thicknesses in accordance with embodiments disclosed herein.

FIG. 5 is a two-dimensional projection similar to FIG. 4 in accordance with embodiments disclosed herein. In FIG. 5, the vessel wall thickness is 0.5 inches. FIG. 5 illustrates shaded regions where the density measurement error is less than 0.0006 gcc and the density error measurement is less than 0.0015 gcc. Using FIG. 5, the optimal position of the gamma-ray detector may be determined given the density in a vessel with a wall thickness of 0.5 inches. In addition, as described above, an operational range of the gamma-ray source/detector system may be determined.

Figure 6:
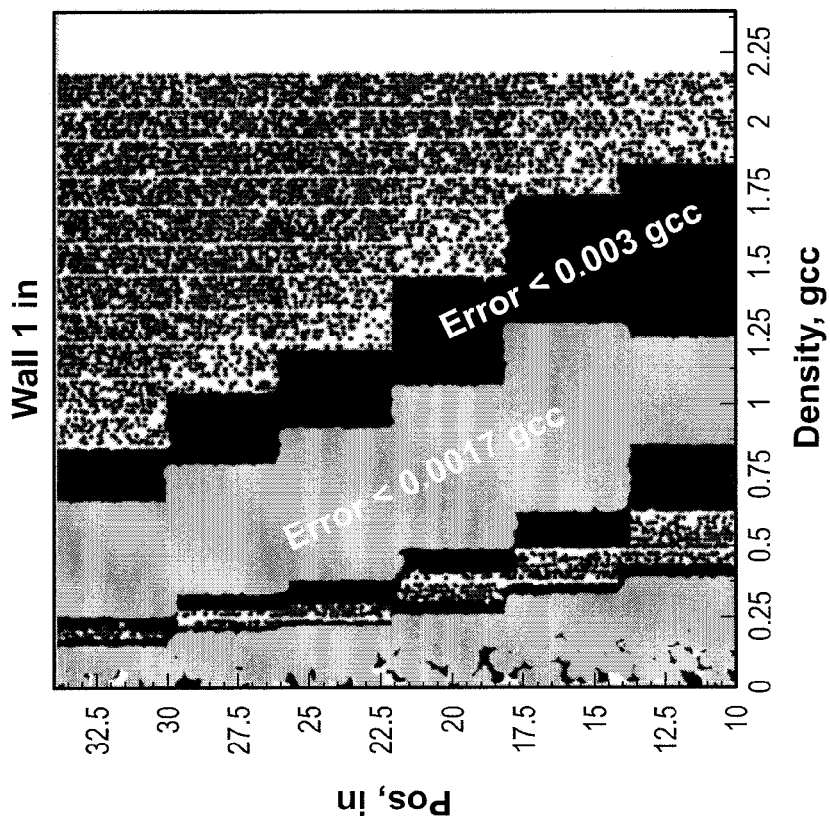

FIG. 6 is a two-dimensional projection similar to FIG. 4 in accordance with embodiments disclosed herein. In FIG. 6, the vessel wall thickness is 1.0 inches. FIG. 6 illustrates shaded regions where the density measurement error is less than 0.003 gcc and the density error measurement is less than 0.0017 gcc. Using FIG. 6, the optimal position of the gamma-ray detector may be determined given the density in a vessel with a wall thickness of 1.0 inches. In addition, an operational range of the gamma-ray source/detector system may be determined.

Figure 7:
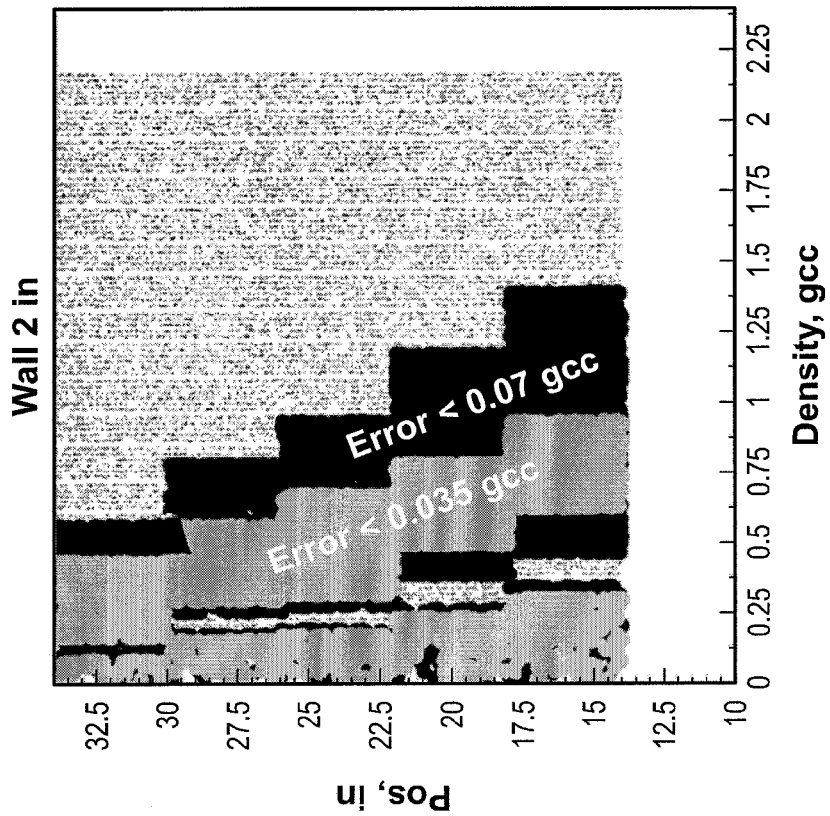

FIG. 7 is a two-dimensional projection similar to FIG. 4 in accordance with embodiments disclosed herein. In FIG. 7, the vessel wall thickness is 2.0 inches. FIG. 7 illustrates shaded regions where the density measurement error is less than 0.07 gcc and the density error measurement is less than 0.035 gcc. Using FIG. 7, the optimal position of the gamma-ray detector may be determined given the density in a vessel with a wall thickness of 2.0 inches. In addition, an operational range of the gamma-ray source/detector system may be determined.

As previously stated, FIGS. 4-7 are two dimensional graphs outlining the error in the measurement of the density of a fluid in a vessel as a function of the density and the position of a gamma-ray detector with respect to a gamma-ray source for different vessel wall thicknesses in accordance with embodiments disclosed herein. As one may expect, the error may be less, or the precision may be higher, for thinner vessel walls as compared to thicker vessel walls. In addition, the operational range of the gamma-ray source/detector system may be greater for thinner vessel walls as compared to thicker vessel walls.

Figure 9:
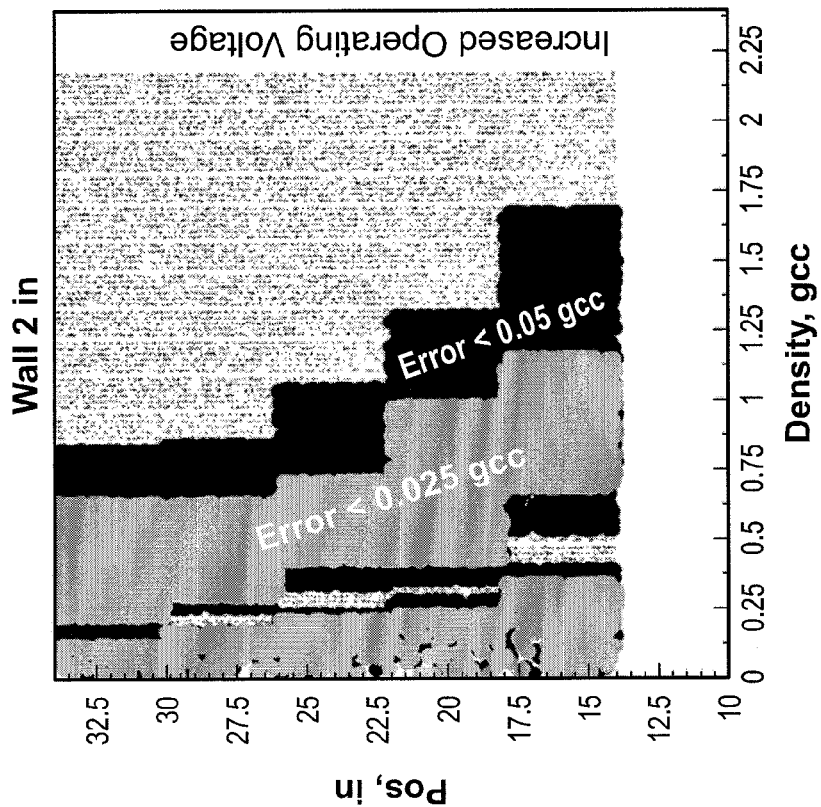
FIGS. 8-9 are two dimensional projections with different vessel wall thicknesses and different detector operating voltages in accordance with embodiments disclosed herein.
Figure 8:
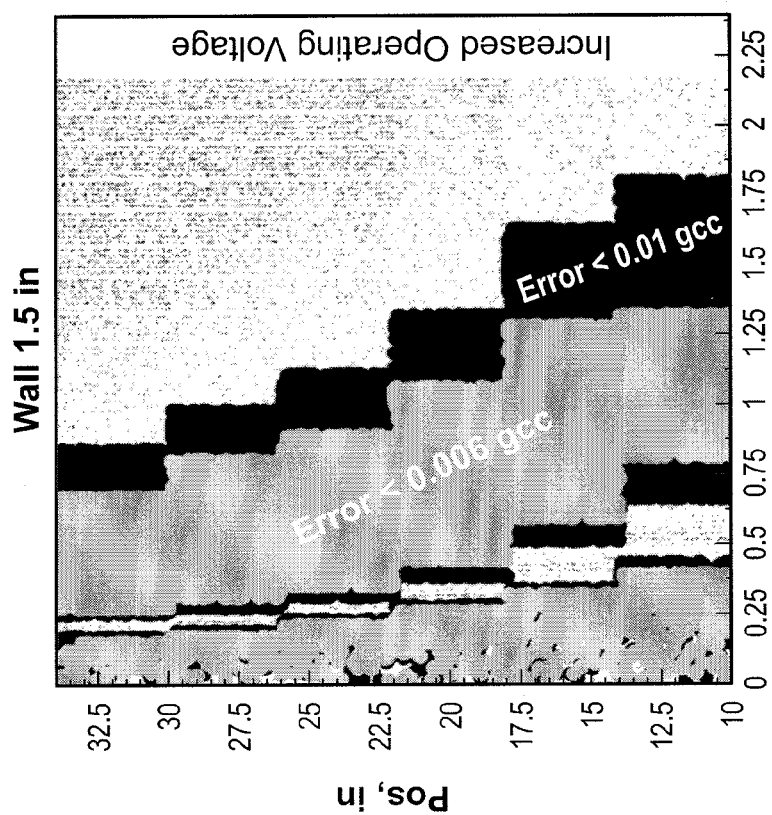

Other methods for improving the precision of the measurement of the density of a fluid in a vessel in accordance with embodiments are disclosed herein. For example, increasing the operating voltage in the gamma-ray detector may marginally improve the precision in the density measurement. Referring now to FIGS. 8 and 9, the results displayed in FIGS. 4 and 7 are reproduced using an increased operating voltage in the gamma-ray detector.

FIG. 8 is a measurement in the error of the density for a vessel wall thickness of 1.5 inches determined using an increased operating voltage in the gamma-ray detector in accordance with embodiments disclosed herein. As shown in comparing the error measurement in FIG. 4 with the error measurement in FIG. 8, there may be an improvement in the precision of the density measurement. FIG. 9 is a measurement in the error of the density for a vessel wall thickness of 2.0 inches determined using an increased operating voltage in the gamma-ray detector in accordance with embodiments disclosed herein. Similar results may be seen when comparing FIG. 7 to FIG. 9.

Figure 10:
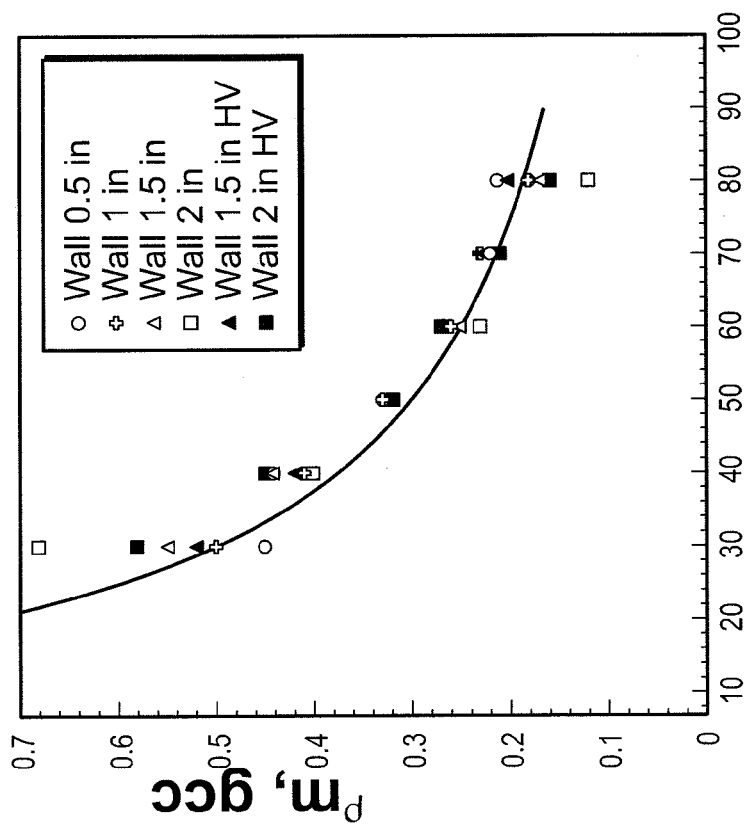
FIG. 10 is a chart of the position of density that has the maximum count rate as a function of detector position in accordance with embodiments disclosed herein.

As discussed in relation to FIG. 2(a), the density at which the counting rate is a maximum is noted as $\rho_m$. FIG. 10 is a chart of the position of density that has the maximum count rate $\rho_m$ as a function of the gamma-ray detector position with respect to the gamma-ray source in accordance with embodiments disclosed herein. The density at which the counting rate is a maximum $\rho_m$, is inversely proportional to the gamma-ray detector position. Referring to FIG. 10, the density at which the counting rate is a maximum $\rho_m$ may be expressed as:

$$\rho_m = \frac{15 \text{ g/cm}^2}{pos} \quad (2)$$

where pos represents the position of the gamma-ray detector with respect to the gamma-ray source as illustrated in FIG. 1. As previously mentioned, the density at which the counting rate is a maximum $\rho_m$ may help to determine the density range when associating the count rate of the gamma-ray detector to the density of the fluid within the vessel.

Figure 11:
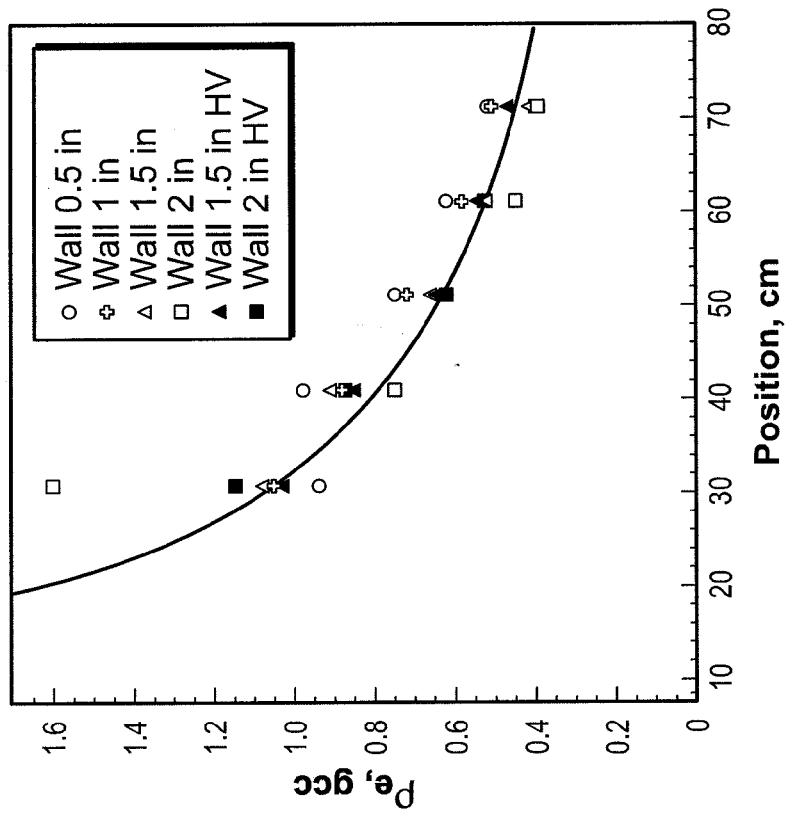
FIG. 11 is a chart of the position of density that has the highest precision as a function of detector position in accordance with embodiments disclosed herein.

As discussed in relation to FIG. 2(b), the density at which the error is smallest $\rho_e$ when the density of the fluid is greater than the density at which the count rate is a maximum $\rho_m$, may be used to represent the optimal position of the gamma-ray detector in relation to the gamma-ray source. FIG. 11 is a chart of the position of density that has the highest precision $\rho_e$ as a function of detector position pos in accordance with embodiments disclosed herein. Referring to FIG. 11, the density that has the highest precision $\rho_e$ may be expressed as:

$$\rho_e = \frac{32 \text{ g/cm}^2}{pos} \quad (3)$$

Accordingly, the position of the gamma-ray detector with respect to the gamma-ray source may be determined by inverting the previous equation:

$$pos = \frac{32 \text{ g/cm}^2}{\rho} \quad (4)$$

Therefore, given an initial estimate of the density of a fluid, as may be known in many industrial applications, the optimal position of a gamma-ray detector with respect to the gamma-ray source may be determined.

Figure 12:
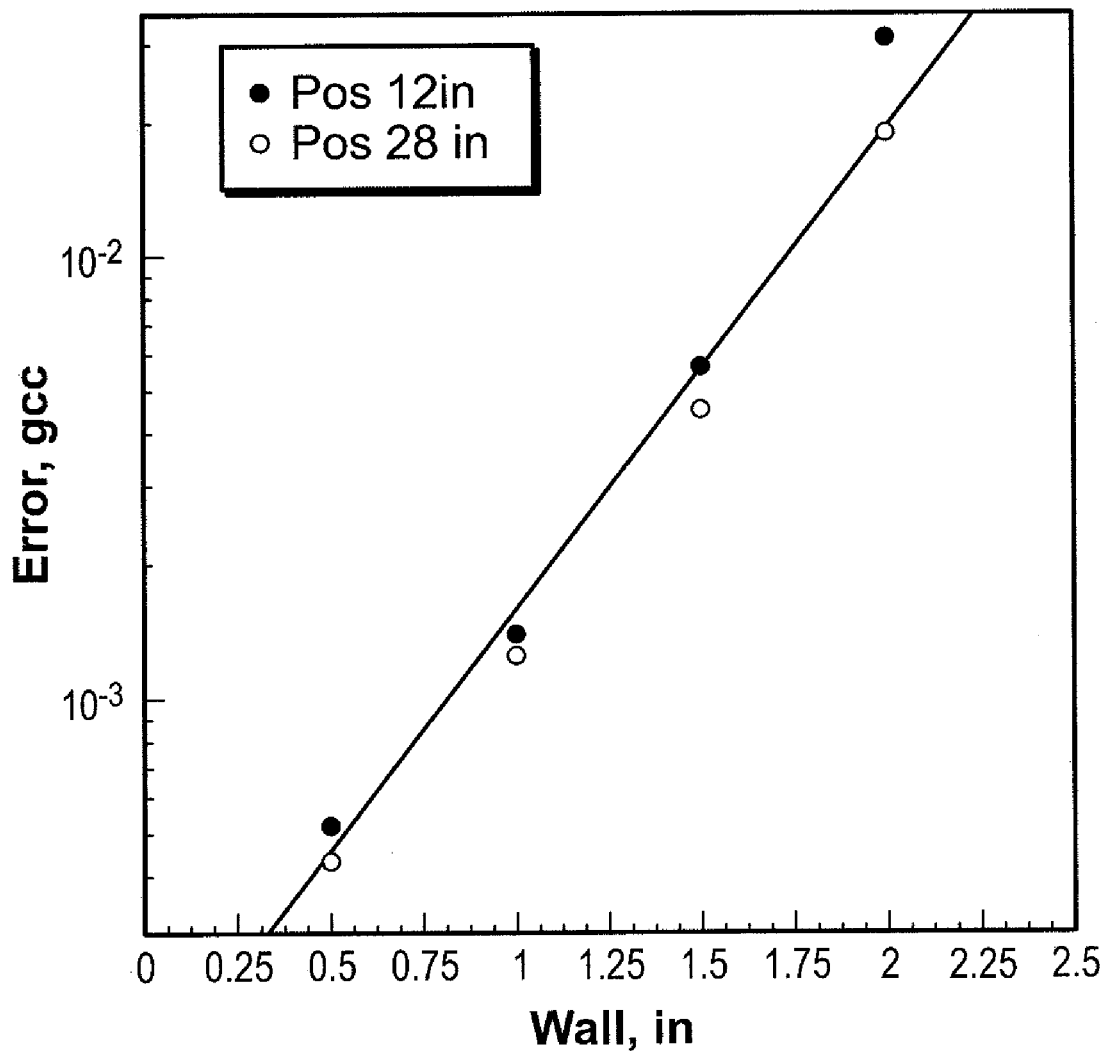
FIG. 12 is a chart of the minimum error as a function of the wall thickness of the vessel for detector positions in accordance with embodiments disclosed herein.

Additionally, as stated previously, the vessel wall thickness may influence the minimal error $\sigma_{min}$ that correlates to the density that has the highest precision $\rho_e$. FIG. 12 is a chart of the minimum error $\sigma_{min}$ as a function of the wall thickness of the vessel for detector positions in accordance with embodiments disclosed herein. The solid circles represent a detector position of 12 inches while the hollow circles represent a detector position of 28 inches. As can be seen, the minimal error $\sigma_{min}$, may be virtually independent of the detector position. In addition, the error $\sigma_{min}$ may scale exponentially with the wall thickness. The minimal error $\sigma_{min}$ may double for every additional 7 mm of thickness in the vessel wall.

Using the above relationships, given the thickness of the wall of a vessel and an estimate of the density of a fluid within the vessel, it may be possible to determine an optimal position of a gamma-ray detector with respect to a gamma-ray source to minimize the error in measuring the density in a backscattered geometry.

Advantageously, the methods disclosed herein may be used to measure positional density gradients on a vessel. Using two or more detectors, the density at different vessel positions may be determined in accordance with embodiments disclosed herein. From the density measurements of the two or more detectors, a density gradient may be determined. Positional density gradients may provide an indication of the degree of settling or mixing that may be occurring in vessel. For example, a vertical positional density gradient may indicate the degree of settling of a solid from a suspension contained in a vessel. As another example, various density gradients may be indicative of static, laminar, or turbulent flow in a vessel. Where vessels form a component in a process, one or more process variables may be manipulated in response to the density profile, such as to increase mixing or to decrease settling rates.

The gamma-ray source may include, for example, cesium-137, americium-241, radium-226, iridium-192, and cobalt-60. In some embodiments, the activity of the source may range from 0.1 mCi to 10 Ci. In other embodiments, the activity of the source may be less than 5 Ci; less than 2 Ci in other embodiments; and less than 1 Ci in yet other embodiments.

Gamma-ray detectors useful in the embodiments disclosed herein may include scintillators such as sodium iodide, cesium iodide, and plastic scintillators. In some embodiments, gamma-ray detectors may include electron photo multiplier tubes (PMT). For example, in the specific embodiments disclosed herein, the gamma ray detector employed two PMTs using an operating voltage of 887 V to 956 V. In the increased voltage measurements, the PMTs used an operating voltage of 1220 V and 1280 V. In other embodiments, gamma-ray detectors may include plastic scintillators, such as a polyvinyl toluene (PVT) scintillator, for example. In yet other embodiments, gamma-ray detectors may include ionization chambers, Geiger counters, proportional counters, semiconductors or other detectors suitable for detection of gamma rays. Where embodiments of the density measurement system disclosed herein contain more than one detector, the detectors may be of the same or different types of gamma-ray detectors.

Gamma-ray backscatter density meters in accordance with embodiments disclosed herein may measure the density of a fluid in a vessel, where the density of the fluid may range from 0 gcc to 7.0 gcc. The effective density range may be from 0.1 gcc to 4.0 gcc in other embodiments; and from 0.2 to 2.0 gcc in yet other embodiments. In other embodiments, one or more gamma-ray backscatter density meters may be used in conjunction with one or more gamma-ray through-transmission density meters.

In yet other various embodiments, the density of a fluid in a vessel may be controlled by manipulating one or more process variables based upon the measured density. For example, where a vessel forms a component in a process, one or more process variables may be manipulated in response to the gamma-ray backscatter density measurement of the fluid in the vessel.

Advantageously, embodiments disclosed herein may provide for a method of optimizing non-contact density measurements by positioning a gamma-ray detector relative to a gamma-ray source so as to detect gamma-ray backscatter.

The non-contact measurement may allow for the measurement of density where the material is hazardous, extremely hot, or where direct contact measurements are not possible. By detecting gamma-ray backscatter, gamma rays do not have to traverse the entire vessel diameter, which may allow for the use of lower intensity gamma-ray sources as well as measurement of density in larger vessels than is currently possible with through-transmission measurements. In addition, optimization of the position of the gamma-ray source detector with respect to the gamma-ray source may increase the precision of the density measurement.

Because embodiments of the gamma-ray backscatter density measurements described herein may allow for use of lower intensity gamma-ray sources, cross-talk between multiple meters used within a production facility may be decreased. The use of lower intensity sources may also allow for use of more than one source and/or detector per vessel, possibly generating a more accurate reflection of fluid density due to multiple measurements. Additionally, because backscatter measurement may allow use of lower intensity gamma-ray sources, production facilities may use additional measuring devices at a single site without incurring the more stringent safety protocols required by state and federal governments for sites having moderate amounts of radioactive material.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining the density of a fluid, the method comprising:
   disposing a gamma-ray source proximate to a vessel having the fluid disposed therein;
   determining an optimal position of a gamma-ray detector with respect to the gamma-ray source;
   disposing a gamma-ray detector at the optimal position; and
   measuring the density of the fluid,
   wherein determining the optimal position comprises:
      determining a wall thickness of the vessel;
      estimating the density of the fluid; and
      selecting the optimal position of the gamma-ray detector based on the wall thickness and estimate of the density of the fluid to maximize the precision of the density measurement.

2. The method of claim 1, wherein the optimal position of the gamma-ray detector is selected to be positioned at 32 $g/cm^2 \div \rho$ with respect to the source, where $\rho$ is the estimate of the density of the fluid.

3. The method of claim 1, further comprising:
   measuring a precision of the measurement of the density of the fluid;
   comparing the estimate of the density of the fluid to the measured density of the fluid;
   determining an estimated precision of the measuring of the density of the fluid based on the vessel wall thickness and optimal position of the gamma-ray detector;
   comparing the precision of the measuring of the density of the fluid to the estimated precision of the measuring of the density of the fluid; and
   adjusting, if necessary, the optimal position of the gamma-ray detector with respect to the gamma-ray source.

4. The method of claim 1, wherein determining the optimal position comprises:
   disposing a gamma-ray detector proximate the gamma-ray source;
   measuring an initial density; and
   selecting the optimal position of the gamma-ray detector based on the wall thickness and the initial density of the fluid to maximize a precision of the density measurement.

5. The method of claim 4, wherein the optimal position of the gamma-ray detector is selected to be positioned at 32 $g/cm^2 \div \rho$ with respect to the source, where $\rho$ is the estimate of the density of the fluid.

6. The method of claim 4, further comprising:
   measuring the precision of the measurement of the density of the fluid;
   determining an estimated precision of the measuring of the density of the fluid based on the vessel wall thickness and optimal position of the gamma-ray detector;
   comparing the precision of the measuring of the density of the fluid to the estimated precision of the measuring of the density of the fluid; and
   adjusting, if necessary, the optimal position of the gamma-ray detector with respect to the gamma-ray source based on the comparison of the precision and the estimated precision.

7. A method for optimizing the position of a gamma-ray detector to determine the density of a fluid in a vessel, the method comprising:
   disposing a gamma-ray source proximate a vessel having the fluid disposed therein;
   determining an optimal position of a gamma-ray detector with respect to the gamma-ray source,
   wherein determining the optimal position comprises:
      determining a wall thickness of the vessel;
      estimating the density of the fluid; and
      selecting the optimal position of the gamma-ray detector based on the wall thickness and estimate of the density of the fluid to maximize the precision of the density measurement;
   disposing at least one gamma-ray detector at the optimal position with respect to the gamma-ray source; and
   measuring the density of the fluid from the gamma-ray detector.

8. The method of claim 7, wherein the optimal position of the gamma-ray detector is selected to be positioned at 32 $g/cm^2 \div \rho$ with respect to the source, where $\rho$ is the estimate of the density of the fluid.

9. The method of claim 7, further comprising:
   comparing the estimate of the density of the fluid to the measured density of the fluid;
   measuring a precision of the measurement of the density of the fluid;
   determining an estimated precision of the measuring of the density of the fluid based on the vessel wall thickness and optimal position of the gamma-ray detector;
   comparing the precision of the measuring of the density of the fluid to the estimated precision of the measuring of the density of the fluid; and
   adjusting the optimal position of the gamma-ray detector with respect to the gamma-ray source.

10. The method of claim 7, wherein determining the optimal position comprises:
    disposing a gamma-ray detector proximate the gamma-ray source;
    measuring an initial density; and selecting the optimal position of the gamma-ray detector based on the wall thickness and the initial density of the fluid to maximize a precision of the density measurement.

11. The method of claim 10, wherein the optimal position of the gamma-ray detector is selected to be positioned at 32 g/cm$^2$÷ρ with respect to the source, where ρ is the estimate of the density of the fluid.

12. The method of claim 10, further comprising:
measuring the precision of the measurement of the density of the fluid;
determining an estimated precision of the measuring of the density of the fluid based on the vessel wall thickness and optimal position of the gamma-ray detector;
comparing the precision of the measuring of the density of the fluid to the estimated precision of the measuring of the density of the fluid; and
adjusting the optimal position of the gamma-ray detector with respect to the gamma-ray source based on the comparison of the precision and the estimated precision.

13. A method for determining the density of a fluid, the method comprising:
disposing a gamma-ray source proximate to a vessel having the fluid disposed therein;
determining an optimal position of a gamma-ray detector with respect to the gamma-ray source;
disposing a gamma-ray detector at the optimal position;
measuring the density of the fluid,
wherein determining the optimal position comprises:
disposing a gamma-ray detector proximate the gamma-ray source;
measuring an initial density; and
selecting the optimal position of the gamma-ray detector based on the wall thickness and the initial density of the fluid to maximize a precision of the density measurement.

14. The method of claim 13, wherein the optimal position of the gamma-ray detector is selected to be positioned at 32 g/cm$^2$÷ρ with respect to the source, where ρ is the estimate of the density of the fluid.

15. The method of claim 13, further comprising:
measuring the precision of the measurement of the density of the fluid;
determining an estimated precision of the measuring of the density of the fluid based on the vessel wall thickness and optimal position of the gamma-ray detector;
comparing the precision of the measuring of the density of the fluid to the estimated precision of the measuring of the density of the fluid; and
adjusting, if necessary, the optimal position of the gamma-ray detector with respect to the gamma-ray source based on the comparison of the precision and the estimated precision.

16. A method for optimizing the position of a gamma-ray detector to determine the density of a fluid in a vessel, the method comprising:
disposing a gamma-ray source proximate a vessel having the fluid disposed therein;
determining an optimal position of a gamma-ray detector with respect to the gamma-ray source;
disposing at least one gamma-ray detector at the optimal position with respect to the gamma-ray source; and
measuring the density of the fluid from the gamma-ray detector;
wherein determining the optimal position comprises:
determining a wall thickness of the vessel;
disposing a gamma-ray detector proximate the gamma-ray source;
measuring an initial density; and
selecting the optimal position of the gamma-ray detector based on the wall thickness and the initial density of the fluid to maximize a precision of the density measurement.

17. The method of claim 16, wherein the optimal position of the gamma-ray detector is selected to be positioned at 32 g/cm$^2$÷ρ with respect to the source, where ρ is the estimate of the density of the fluid.

18. The method of claim 16, further comprising:
measuring the precision of the measurement of the density of the fluid;
determining an estimated precision of the measuring of the density of the fluid based on the vessel wall thickness and optimal position of the gamma-ray detector;
comparing the precision of the measuring of the density of the fluid to the estimated precision of the measuring of the density of the fluid; and
adjusting the optimal position of the gamma-ray detector with respect to the gamma-ray source based on the comparison of the precision and the estimated precision.

* * * * *